United States Patent [19]

Baker

[11] Patent Number: 5,497,913

[45] Date of Patent: Mar. 12, 1996

[54] MIXING BAG ARRANGEMENT AND METHOD

[75] Inventor: Denny D. Baker, 1331 Piper Dr., New Brighton, Minn. 55112

[73] Assignees: Denny D. Baker, New Brighton; Richard Mrocek; Sharon Mrocek, both of White Bear Lk., all of Minn.

[21] Appl. No.: 167,780

[22] Filed: Dec. 15, 1993

[51] Int. Cl.[6] ................................. B65D 35/28
[52] U.S. Cl. ................... 222/102; 222/541.6; 383/37
[58] Field of Search ................... 222/101, 102, 222/158, 541; 383/37, 77

[56] References Cited

U.S. PATENT DOCUMENTS

| | | | |
|---|---|---|---|
| D. 221,214 | 7/1971 | MacManus | D9/194 |
| D. 264,427 | 5/1982 | Richards | D9/305 |
| 717,964 | 1/1903 | Batdorf | 229/87.2 |
| 1,237,930 | 8/1917 | Malvern et al. | 383/6 |
| 1,676,102 | 7/1928 | Lynam | 100/211 |
| 2,019,197 | 10/1935 | Spanel | 150/1 |
| 2,707,581 | 5/1955 | Kaplan et al. | 222/541 |
| 2,956,710 | 10/1960 | O'Connor | 222/541 |
| 2,962,192 | 11/1960 | Volckening | 222/541 |
| 3,052,399 | 9/1962 | Brown | 229/85 |
| 3,186,625 | 6/1965 | Mead et al. | 229/53 |
| 3,189,227 | 6/1965 | Hobbs et al. | 222/94 |
| 3,199,437 | 8/1965 | Nelson | 99/317 |
| 3,278,085 | 10/1966 | Brown | 222/541 |
| 3,483,061 | 12/1969 | Takahashi et al. | 383/37 |
| 3,583,558 | 6/1971 | Davis | 206/58 |
| 3,946,904 | 3/1976 | Mulakala | 222/102 |
| 3,961,743 | 6/1976 | Hollowell | 383/37 |
| 3,979,050 | 9/1976 | Cilia | 383/37 |
| 4,016,975 | 4/1977 | Hammer | 206/390 |
| 4,077,151 | 3/1978 | Johnson | 43/43.12 |
| 4,345,712 | 8/1982 | Gim | 383/37 |
| 4,445,230 | 4/1984 | Spadaro | 383/7 |
| 4,576,316 | 3/1986 | Foster | 222/541 |
| 4,627,551 | 12/1986 | Kopp | 222/102 |
| 4,709,400 | 11/1987 | Bruno | 383/77 |
| 4,759,472 | 7/1988 | Strenger | 222/541 |
| 4,797,309 | 1/1989 | Kammerer et al. | 222/541 |
| 4,890,736 | 1/1990 | Greyvenstein | 206/390 |
| 4,921,137 | 5/1990 | Heijenga | 222/541 |
| 4,938,608 | 7/1990 | Espinosa | 383/37 |

FOREIGN PATENT DOCUMENTS 4101902  4/1992  Japan ..................... 383/37

OTHER PUBLICATIONS

Cadco catalog, front cover page, pp. 1–10 and back cover page, dated Apr., 1990, Exhibit A.

Catalog page, "Investment Equipment," p. 68, labeled Exhibit B.

Bond Tile Products, "High Roller Dispensing System For Light weight Body Fillers", Oct. 2, 1985, pp. 1 & 2.

*Primary Examiner*—Andres Kashnikow
*Assistant Examiner*—Lisa Douglas
*Attorney, Agent, or Firm*—Merchant, Gould, Smith, Edell, Welter & Schmidt

[57] ABSTRACT

A mixing bag and method is provided for mixing ingredients and dispensing the mixed ingredients. The bottom of the bag has a converging tip. The top edge of the bag defines an open end and includes a reciprocally shaped edge to the bottom edge so that the bags can be cut from a continuous tube of material. The bag is filled with ingredients to be mixed through the open end and the ingredients are mixed by kneading the bag with the hands. The bag is closed prior to mixing. Once the ingredients are sufficiently mixed, the converging tip of the bag is removed and the contents are squeezed out from the bag. Prior to mixing, a closure device, or a twist applied to the bag, closes off the open end of the bag. Particular materials to be mixed are dental alginates and stones for making dental impressions. Other ingredients besides dental products can be mixed in the bag.

12 Claims, 7 Drawing Sheets

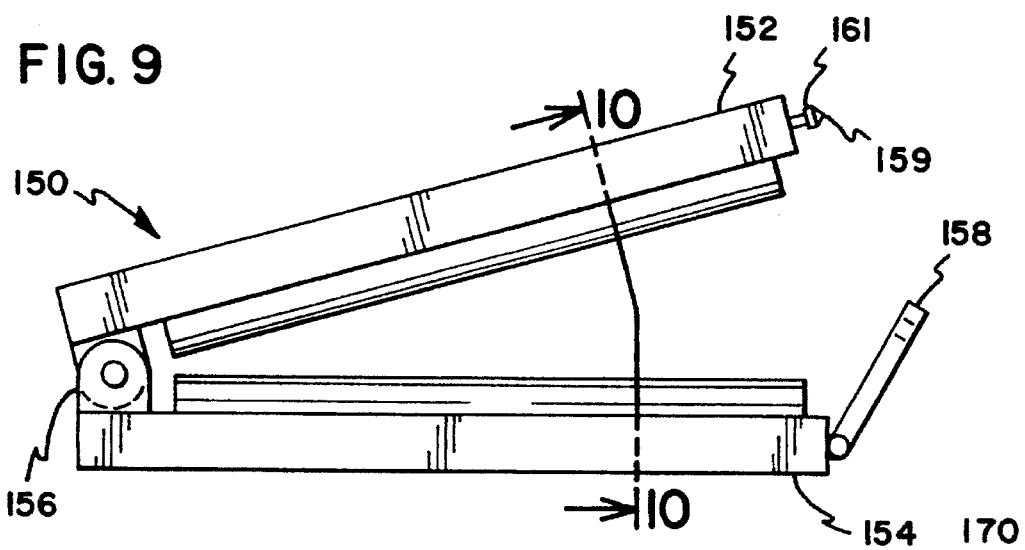
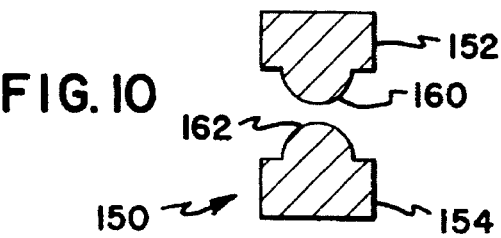
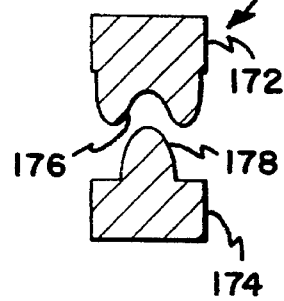
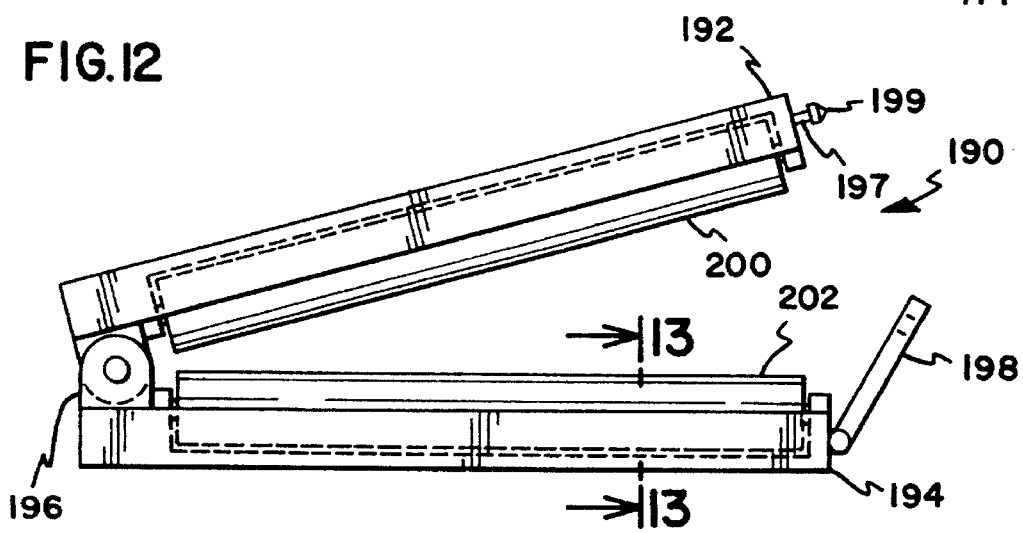
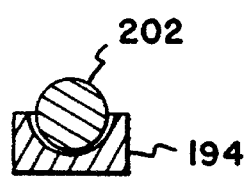

MIXING BAG ARRANGEMENT AND METHOD

FIELD OF THE INVENTION

The present invention relates to mixing bags and methods of mixing and dispensing materials, such as hydrophilic impression materials.

BACKGROUND OF THE INVENTION

Various industries require that materials be mixed prior to usage. For example, dentists often need to prepare hardenable construction materials for making impressions of the teeth and other portions of the mouth for study and treatment. Dentists prepare a hydrophilic impression material, such as alginate, for use in making the impression. The alginate is supplied in a powdered form and water is added by the dentist or dental assistant to prepare the material for use. Once the water is added and the ingredients are mixed together, the alginate sets quickly, such as within about 30–90 seconds from the time the water is added. Before the alginate sets, the alginate is typically placed on a tray and then the alginate is positioned against the portion of the mouth desired for making the impression. Once the alginate sufficiently sets in the position against the mouth, the alginate forms a hardened structure containing a reverse image impression of the portion of the mouth.

From this alginate impression, the dentists will often make an actual model or mold of the mouth parts by molding from the alginate impression. Another material called "stone", more rigid than alginate, may be utilized for making the mold. Like alginate, stone is supplied in a powdered form, water is added, and then the materials are mixed together and positioned around the impression in the alginate. Once the stone sets, the alginate impression is removed and the stone mold is finished.

Various methods of mixing alginate and/or stone are known. One method utilizes a rubber bowl and a spatula for mixing the powder and the water manually. This method is awkward and takes a high amount of skill to correctly mix the ingredients before the materials set and without producing excessively large air bubbles, which can cause defects in the impression of mold. For alginate, the mixed material must then be manually scooped from the bowl with the spatula to the tray in the appropriate amount for insertion into the mouth for holding the alginate against the desired portion of the mouth. Further, the bowl and the spatula must be cleaned afterwards and disinfected before subsequent reuse.

Another method of mixing alginate and/or stone is to supply a mechanism for spinning a bowl while the operator manually manipulates a spatula to mix the materials. This method is messy since the bowl and spatula must be cleaned after use. This method also requires a high amount of skill to appropriately mix the ingredients in a short amount of time before the material sets. Further, these tools must be disinfected prior to subsequent use. In addition, the mechanism for spinning the bowl increases the costs to the dentist.

A further method of mixing the materials utilizes a self-contained mixer for mixing the materials within an enclosed chamber of a rigid container, much like a conventional blender. A spinning blade member rotates to mix the materials within the rigid container. Not only is the mixer costly, but the components must be cleaned after each use and disinfected.

Other industries which utilize mixers and various methods of mixing ingredients include other medical fields, engineering, biology, and art. In many of these industries, materials are mixed for making impressions where the cost, the ease of use, and the quality of the mixed materials are significant concerns. Food preparation is another area where there is a need for properly mixed powdered materials and liquids.

There is a need for mixing bag arrangements and methods for mixing materials which addresses at least some of the above problems and other problems.

SUMMARY OF THE INVENTION

The present invention relates to a mixing bag arrangement comprising a first panel and a second panel interconnected along the edges of each panel. A first edge portion of the first panel and the second panel define an open end of the bag arrangement. The bottom edge defines a converging tip region including a line of weakening, such as a line of perforations through the first panel and through the second panel defining a tear line to open the bag arrangement. The open end preferably has a reciprocal shape to the bottom edge.

The mixing bag arrangement receives ingredients to be mixed. Once the ingredients are placed within the bag, the open end is closed off and the first and second panels are squeezed together and manipulated with the hands to mix the ingredients. Once the ingredients are sufficiently mixed, the converging tip is removed along the line of weakening or otherwise opened. The first and second panels are squeezed together to expel the contents of the bag through the opening formed in the tip region.

Various shapes to the bottom and top edges of the bag are anticipated. Reciprocally shaped edges permit the bag arrangements to be made from continuous roll stock with the bags formed successively. The bottom edge can be formed by a heat seal extending from one side edge to the opposite side edge.

Additional perforations may be provided in at least one of the first panel and the second panel to facilitate the expulsion of entrapped air during mixing.

Bag closure structure may be provided for closing off the open end of the bag arrangement during mixing and dispensing. Preferably, the bag closure structure is slidable toward the converging tip region to facilitate dispensing of the contents of the bag arrangement once the contents are mixed and the converging tip region has been removed along the line of weakening or otherwise opened. Various bag closure structures are anticipated including a ring arrangement with an aperture for receiving the bag arrangement. A hinged closure with snap lock means provides an alternative structure for closing the bag arrangement.

Preferably, the panel arrangement is made of a thin polymeric material which is at least partially transparent to visible light.

Another aspect of the invention relates to providing a panel arrangement defining an open end for use in filling the bag with ingredients to be mixed. A slidable closure structure is provided for closing the open end of the panel arrangement and for moving relative to the panel arrangement away from the open end of the panel arrangement. Various slidable closure structures are anticipated, including a ring closure or a hinged closure, including a roller. The slidable closure structure is usable to dispense the mixed ingredients from the panel arrangement through an opening formed therein as the slidable closure structure is moved relative to the panel arrangement.

The present invention also relates to a method of mixing ingredients in a mixing bag comprising the steps of filling the mixing bag with the ingredients to be mixed through an open end of the bag, closing the open end of the bag to define an enclosed chamber including the ingredients to be mixed, mixing the ingredients by squeezing the bag, forming an opening in the bag at an opposite end to the open end and squeezing the bag to dispense the mixed ingredients through the opening.

Preferably, the ingredients include powdered construction material. In the preferred method, the opening in the mixing bag is formed by tearing the mixing bag across a first panel and a second panel along a line of perforations. The open end of the bag is preferably closed by adding a closure device or twisting the bag closed. The closure device is slidable relative to the bag to facilitate dispensing of the mixed ingredients. Preferably, air is expelled from the mixing bag by perforations provided in the bag.

BRIEF DESCRIPTION OF THE DRAWINGS

FIG. 9 is an enlarged side view of a third closure device;

FIG. 10 is a cross-sectional end view of a portion of the third closure device of FIG. 9 taken along lines 10—10;

FIG. 11 is an enlarged cross-sectional end view of a portion of a fourth closure device;

FIG. 12 is an enlarged side view of a fifth closure device;

FIG. 13 is a cross-sectional end view of a portion of the fifth closure device of FIG. 12 taken along lines 13—13;

DETAILED DESCRIPTION OF THE PREFERRED EMBODIMENTS

Figure 1:
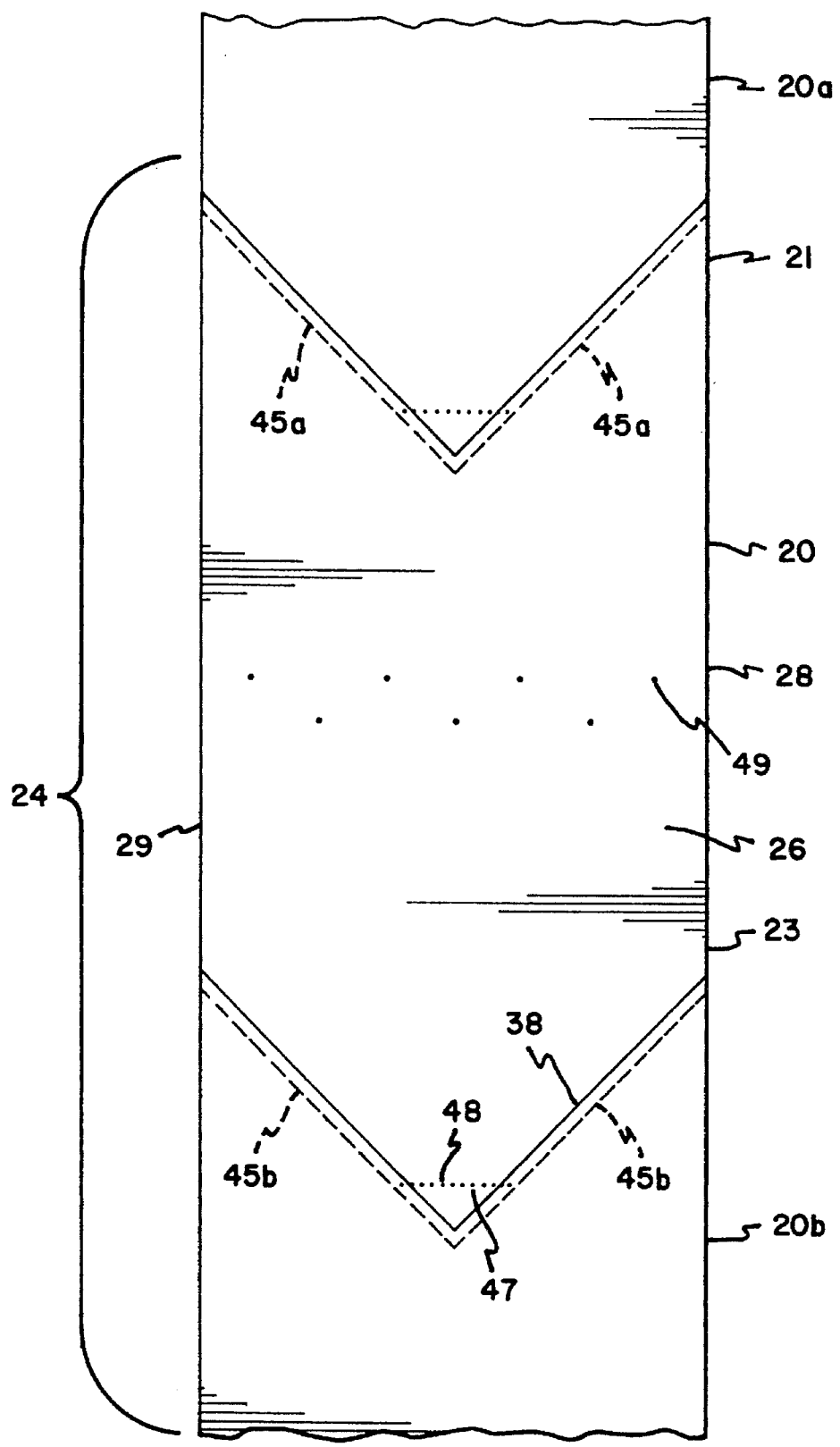
FIG. 1 shows a mixing bag arrangement according to the present invention interconnected with a plurality of other mixing bag arrangements in a continuous roll stock.
Figure 2:
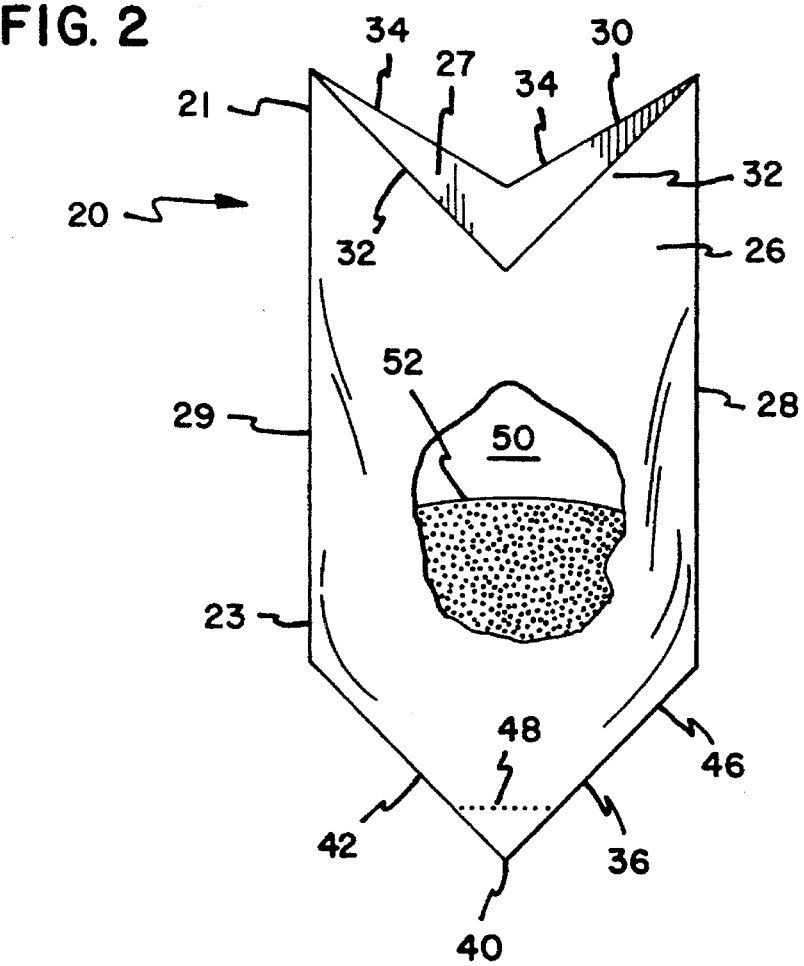
FIG. 2 is a perspective view on a reduced scale of the mixing bag arrangement shown in FIG. 1 showing a portion of the ingredients inside.

Referring now to FIGS. 1 and 2, a mixing bag 20 according to the present invention is shown. In FIG. 1, bag 20 is interconnected to an identical bag 20a on one end 21 and an identical bag 20b on an opposite end 23. FIG. 1 illustrates mixing bag 20 making up a portion of a roll stock arrangement 24 for manufacturing and dispensing individual bags 20. In using roll stock arrangement 24, first bag 20b would be separated from second bag 20 at the desired time, as by tearing along perforation line 45b. Similarly, second bag 20 would be separated from third bag 20a, as by tearing along perforation line 45a.

As shown in FIG. 2, bag 20 includes a first panel 26 and a second panel 27 oppositely disposed from one another. First panel 26 and second panel 27 are interconnected along first linear side edge 28 and second linear side edge 29. In the embodiment shown, side edges 28, 29 do not define any seams since bag 20 is made from continuous roll stock. However, one or more of side edges 28, 29 could include a seam wherein first panel 26 is heat sealably joined to second panel 27 during manufacture, for example.

At end 21, bag 20 includes an open top end 30 defined by a V-shaped first edge portion 32 of first panel 26 and a V-shaped second edge portion 34 of second panel 27. At opposite bottom end 23 of bag 20 is a closed end 36 formed by a heat seal 38 wherein front panel 26 is joined to second panel 27. Closed end 36 includes a first linear edge portion 42 and a second linear edge portion 46 which intersect at tip 40 and define a V-shape. Generally, first edge portion 42, second edge portion 46, and tip 40 define a converging tip structure. To facilitate efficient manufacture and use of materials, perforation lines 45a, 45b for separating the bags from one another are identically shaped.

Bag 20 defines a chamber 50 for receiving ingredients 52 via open top end 30 to be mixed during use. During mixing, open top end 30 is closed off to prevent the escape of ingredients 52 during mixing. During the actual hand mixing operation, the various edges and panel portions of bag 20 are squeezed together or otherwise manipulated successively or simultaneously in a variety of different manners to mix or knead the ingredients 52 by hand in chamber 50.

Figure 14:
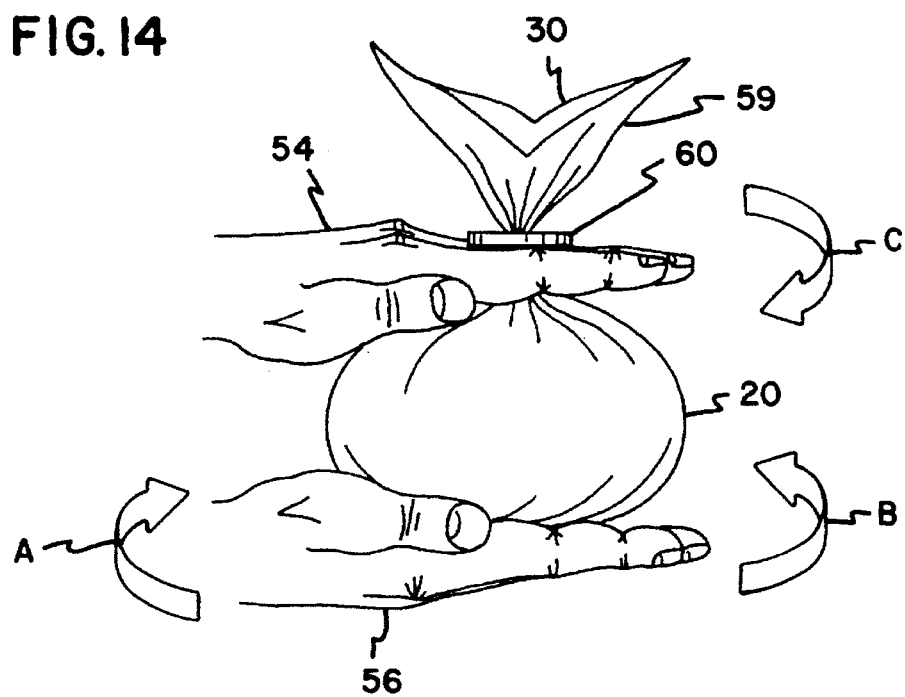
FIG. 14 shows the mixing bag arrangement of FIG. 2 with the first closure device of FIGS. 3 and 4 during mixing.

Referring now to FIG. 14, bag 20 is shown during the mixing operation with an operator's first hand 54 and second hand 56 squeezing bag 20 therebetween in the directions of arrows A, B, C to mix ingredients 52 contained within bag 20. In particular, hands 54, 56 can be pushed toward one another, the fingers of each hand 54, 56 can be moved toward the base and/or thumb of each hand in the general manner of forming a fist, and/or hands 54, 56 can be moved in circular motions relative to the palms of one another.

As shown in FIG. 14, a closure device 60 closes off open end 30 of bag 20 by passing bag 20 through a constricted passage. During mixing, flap portion 59 of bag 20 is positioned between two of the fingers of hand 54.

Figure 3:
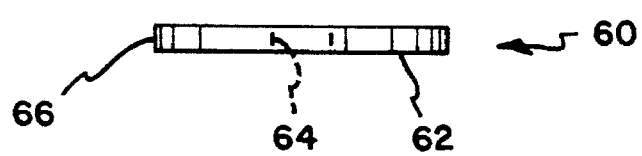
FIG. 3 is an enlarged side view of a first closure device for closing the open end of the mixing bag arrangement.
Figure 4:
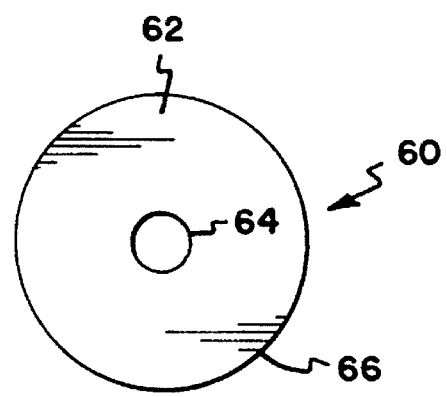
FIG. 4 is an end view of the first closure device shown in FIG. 3.
Figure 15:
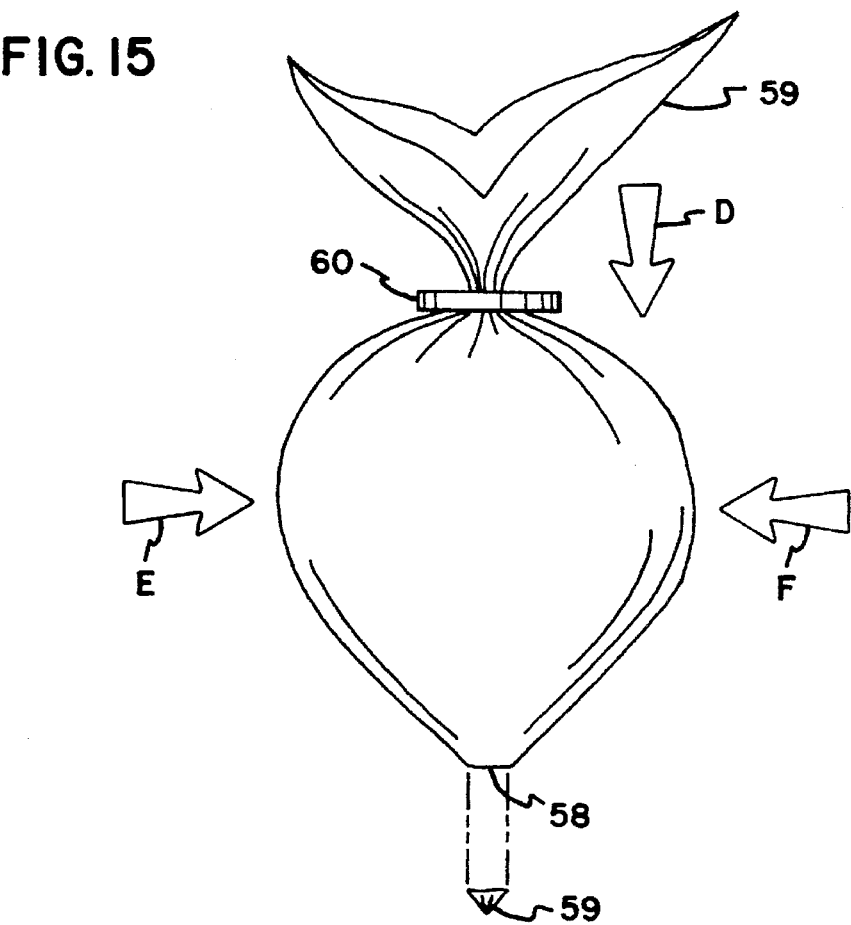
FIG. 15 shows the mixing bag arrangement of FIG. 14 ready for dispensing on an enlarged scale.

Referring now to FIGS. 3 and 4, closure device 60 (first closure device) is shown in greater detail. First closure device 60 includes a plate portion 62 defining an aperture 64 and an outer periphery 66. Aperture 64 is sufficiently large to receive an entire cross section of bag 20 in a bunched configuration as shown in FIG. 14. Flap 59 is threaded through aperture 64 during use. Plate portion 62 is sufficiently large to provide a convenient gripping and/or pushing surface for applying a force by the hand in the direction of arrow D in FIG. 15 to push the mixed ingredients from an interior of bag 20 out through an opening 58 formed in bag 20 after mixing. Aperture 64 is sized sufficiently small to provide a constricted opening to permit the mixed ingredients to be dispensed from bag 20 during the sliding motion of closure device 60. Flap 59 is held in the other hand while the force is applied to closure device 60. Alternatively, or in combination with device 60, the mixed ingredients can be squeezed by hand from bag 20 in the direction of arrows D, E and/or F.

Figure 5:
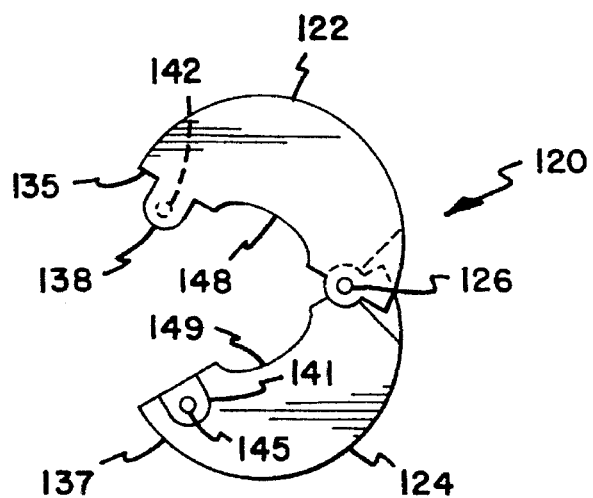
FIG. 5 is an enlarged side view of a second closure device in an open position.
Figure 6:
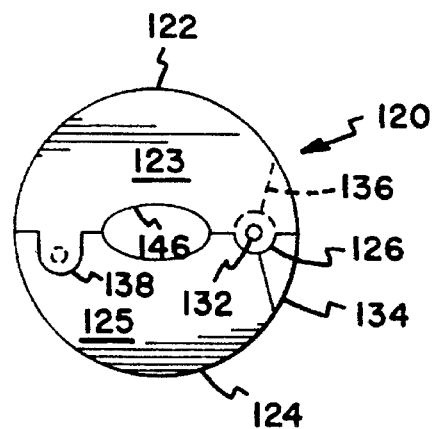
FIG. 6 is a side view of the second closure device of FIG. 5 in a closed position.
Figure 7:
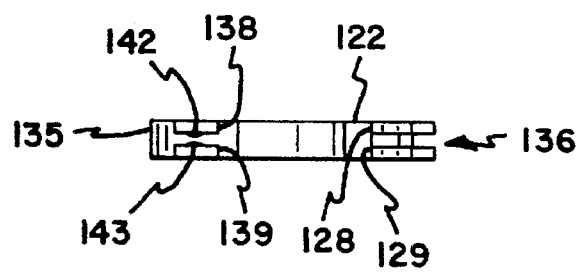
FIG. 7 is an end view of a first half of the second closure device.
Figure 8:
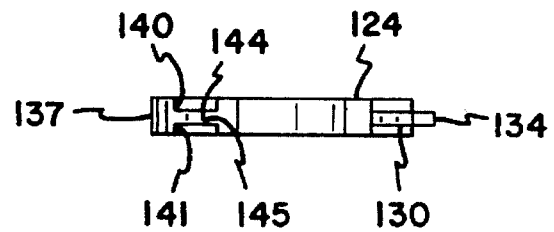
FIG. 8 is an end view of a second half of the second closure device.

Referring now to FIGS. 5–8, an alternative closure device 120 (second closure device) is shown. Second closure device 120 includes a first half 122 and a second half 124. A hinge 126 hingedly attaches first half 122 to second half 124. Two ears 128, 129 extend from first half 122. A single ear 130 extends from second half 124. Ears 128, 129, 130 each include a passage which cooperates with pin 132 to form hinge 126. Projection 134 adjacent hinge 126 fits within recess 136 adjacent hinge 126 when second closure device 120 is in the open position as shown in FIG. 5.

To hold second closure device 120 in the closed position, a snap arrangement is provided to releasably lock first half 122 to second half 124. The snap arrangement includes two opposed fingers 138, 139 projecting from first half 122 at end 135 disposed away from hinge 126. First and second depressions 140, 141 are formed in second half 124 adjacent end 137 disposed away from hinge 126. Bumps 142, 143 extend toward each other from fingers 138, 139, respectively. Bumps 142, 143 cooperate with small recesses 144, 145 in depressions 140, 141, respectively, of second half 124 to releasably hold second closure device 120 in the closed position.

For receiving bag 20 in a constricted manner, a passage 146 is formed by first recess half 148 and second recess half 149 when second closure device 120 is in the closed position. Hinge 126 permits convenient placement of bag 20 in passage 146 when second closure device is in the open position shown in FIG. 5. Once bag 20 is positioned adjacent each recess half 148, 149, closure device 120 is placed in the closed position shown in FIG. 6. During use, bag 20 is squeezed between first half 122 and second half 124 to close the open end 30 of bag 20. Second closure device 120 is used in place of closure device 60 shown in FIG. 14, and avoids the step of threading flap 59 through a constricted opening. After mixing, a force can be applied by the hand on plate portions 125, 127 of second closure device 120 to move second closure device 120 toward the opening 58 formed in bag 20 to dispense the mixed ingredients. Alternatively, closure device 120 can be used only as a closure device for closing open top end 30 of bag 20, and the contents of bag 20 would be squeezed out by hand. For a bag 20 4 inches wide and made from 1 mil polyethylene, passage 146 sized at ¼ inches by ¾ inches works well.

Referring now to FIGS. 9 and 10, a third alternative closure device 150 is shown. Third closure device 150 includes a first bar 152 hingedly attached to second bar 154 at hinge 156. Snap lock structure, such as including a flap 158 and a pin 159 with an enlarged head 161, permits first bar 152 to be held against or adjacent to second bar 154. During use, bag 20 is squeezed between first bar 152 and second bar 154 to close the open end 30 of bag 20. After mixing, a force can be applied to move closure device 150 toward the opening 58 formed in bag 20 to dispense the ingredients. First bar 152 and second bar 152 include an integrally formed tip 160, 162 on each bar. Flap 158 releases from pin 159 by a reverse force to the force applied to lock flap 158 to pin 159.

Referring now to FIG. 11, a fourth alternative closure device 170 is shown. Closure device 170 includes a first bar 172 and a second bar 174, which are hingedly attached to one another, such as in accordance with closure device 150 shown in FIGS. 9 and 10. First bar 172 includes an integrally formed recess 176 for receipt of tip 178 of second bar 174. The cross-sections shown in FIG. 11 extend linearly in approximately the same manner as in FIGS. 9 and 10.

Referring now to FIGS. 12 and 13, a fifth alternative closure device 190 is shown. Closure device 190 includes a first bar 192 hingedly attached to second bar 194 at hinge 196. A snap lock arrangement with flap 198 and a pin 197 with an enlarged head 199 permits snap locking similar to the lock arrangement of closure device 150 is provided. Instead of integral tips 160, 162 as in closure device 150, closure device 190 includes a rotatable roller 200 associated with first bar 192 and a rotatable roller 202 associated with second bar 194. During use, first bar 192 and second bar 194 are brought together to squeeze bag 20 therebetween to close off open top end 30. After mixing, closure 190 can be pushed toward an opening formed in bag 20 to dispense the mixed ingredients. Rollers 200, 202 facilitate movement of closure device 190 toward the opening 58 formed in bag 20.

Closure devices 120, 150, 190 are shown on an enlarged scale relative to closure devices 60, 120. Generally, closure devices 60, 120, 150, 150, 190 are sized to be conveniently grasped by the hand, and are sized to appropriately constrict bag 20 to permit mixing and/or dispensing of the contents of bag 20. A length of 2 to 2 and ½ inches works well. Preferably, closure devices 60, 120, 150, 150, 190 are constructed from molded plastic.

Referring again to FIG. 1, a line of weakening 47 is provided across first panel 26 and second panel 27 for tearing open bag 20 for dispensing its contents. In the preferred embodiment shown, perforations 48 are provided in first panel 26 and second panel 27 extending from first edge portion 36 to second edge portion 42 of closed end 36. Preferably, perforations 48 are configured in a line across closed end 36. Perforations 48 provide a weakened region facilitating tearing of first panel 26 and second panel 27 to create an opening 58 by removal of tip 59 (See FIG. 15) for dispensing the mixed contents from bag 20. Instead of perforations 48, a score line may be provided to create a weakened region for opening bag 20. In that case, the score line would be provided in both first panel 26 and second panel 27.

As shown in FIG. 1, second perforations 49 are provided to allow air in bag 20 to escape from bag 20 during mixing. Second perforations 49, generally centrally located in bag 20, are preferred since second perforations 49 permit an escape of air from within bag 20 during mixing should any air become trapped inside. An escape of air during mixing facilitates better mixing of the ingredients and less entrapped air bubbles within the mixture.

Preferably, second perforations 49 are sufficiently small such that little or none of the ingredients in the bag arrangement can escape during mixing. In the case of alginate, once a material has begun mixing, a rubbery material is formed containing the ingredients in a single mass.

Second perforations 49 are preferably staggered in two or more lines in the manner shown in FIG. 1 to maintain the integrity of first and second panels 26, 27 during mixing.

Referring again to FIGS. 14 and 15, bag 20 is shown during use. In FIG. 14, the ingredients are being mixed. Once the ingredients are sufficiently mixed, tip portion 59 is removed from bag 20 along perforation line 48. Opening 58 is formed for dispensing the mixed contents of bag 20. The ingredients from bag 20 can be dispensed through opening 58 via a squeezing motion applied to bag 20 as shown in FIG. 10 along arrows D, E and F. Alternatively, or in combination with the hand action along arrows E and F, the contents of bag 20 can be dispensed through opening 58 via a sliding movement of one of the closure devices 60, 120, 150, 170, 190 or other closure device, closing off open end 30 of bag 20. Movement of closure device 60 is in the direction of arrow D to dispense from opening 58 in FIG. 15. Once the materials are dispensed from bag 20, bag 20 is discarded.

One preferred method of mixing includes mixing dental alginate and/or stone. The alginate/stone are made by mixing powdered alginate/stone and water within bag 20 according to the present invention. Once these ingredients are mixed, the material is dispensed via opening 58 onto the desired location by the operator. In accordance with the preferred method, opening 58 can be formed by tearing along perforation line 48 if provided. Alternatively, the converging tip structure of closed end 36 of bag 20 can be torn away if a score line or other line of weakening is provided. If no line of weakening is provided, bag 20 can be cut with scissors or other sharp instrument or otherwise torn to form an opening to dispense the contents. It is to be appreciated that it is possible to form the opening for dispensing in only one of panels 26, 27, although it is preferred to form the opening by removing a portion of both panels 26, 27 adjacent tip 40.

Twisting by hand of bag 20 to close open top end 30 to form a constricted twisted portion is an alternative to applying one of closure devices 60, 120, 150, 170, 190. In that case, the free end of bag 20 is held to maintain the twisted portion of bag 20 in the constricted state during mixing and dispensing.

Figure 16:
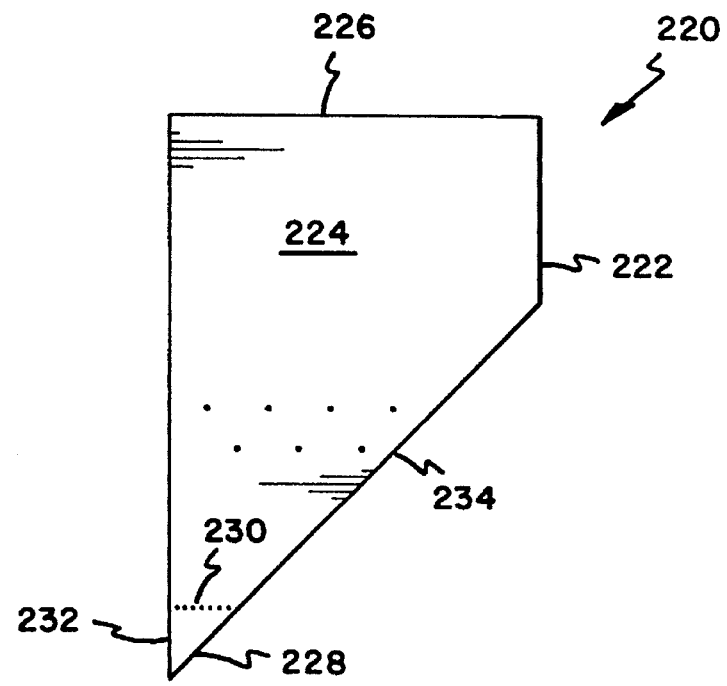
FIG. 16 is a first alternative embodiment of the bag arrangement shown in FIG. 1.

Referring now to FIG. 16, a first alternative bag 220 (second bag 220) is shown. A peripheral edge 222 joins a front panel 224 to a back panel (not visible) along peripheral edge 222 except along top linear edge 226. Peripheral edge 222 defines a converging tip 228. Perforation line 230 through both panels permits tip portion 232 to be torn away from a remainder of bag 220 for dispensing of the contents of bag 220. Bag 220 is heat sealed at linear edge 234. Roll stock can be utilized by alternating the direction of bag 220.

Figure 17:
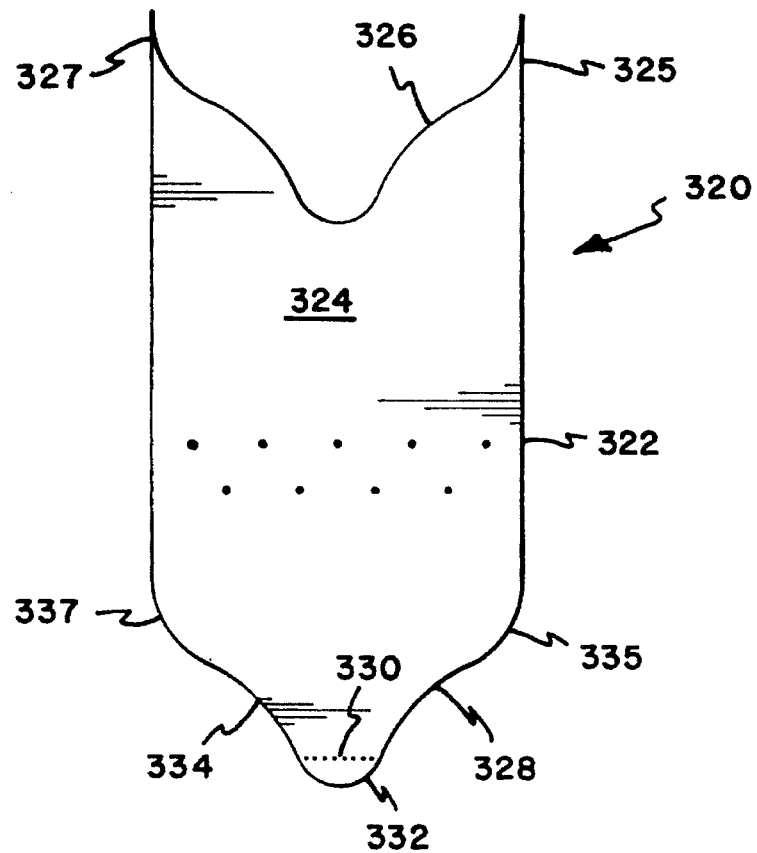
FIG. 17 is a second alternative embodiment of a bag arrangement to the arrangement shown in FIG. 1.

Referring now to FIG. 17, a second alternative bag 320 is shown. A peripheral edge 322 joins a front panel 324 to a back panel (not visible) along peripheral edge 322 except along top edge 326 which extends between points 325, 327. Peripheral edge 322 defines a converging tip 328. Perforation line 330 through both panels permits tip 332 to be torn away from a remainder of bag 320 for dispensing of the contents of bag 320. Bottom edge 334 defines a reciprocal shape to top edge 326 to permit utilization of roll stock. Bag 320 is heat sealed at bottom edge 334 between points 335, 337.

Bottom edge 334 between points 335, 337 and top edge between points 325, 327 of bag 320 defines a smooth curve in an alternative configuration to edges 32, 34, 42, 46 in bag 20. Both bags 20, 320 are symmetrical about the longitudinal axis, with a centrally located tip 40, 332. Other shapes are anticipated.

Bags 20, 220, 320 are preferred in that dead corners are not present where unmixed or improperly mixed ingredients could become trapped during mixing. Generally, it is believed a dead corner may be more likely to form when a 90 degree or less internal corner is formed.

Figure 18:
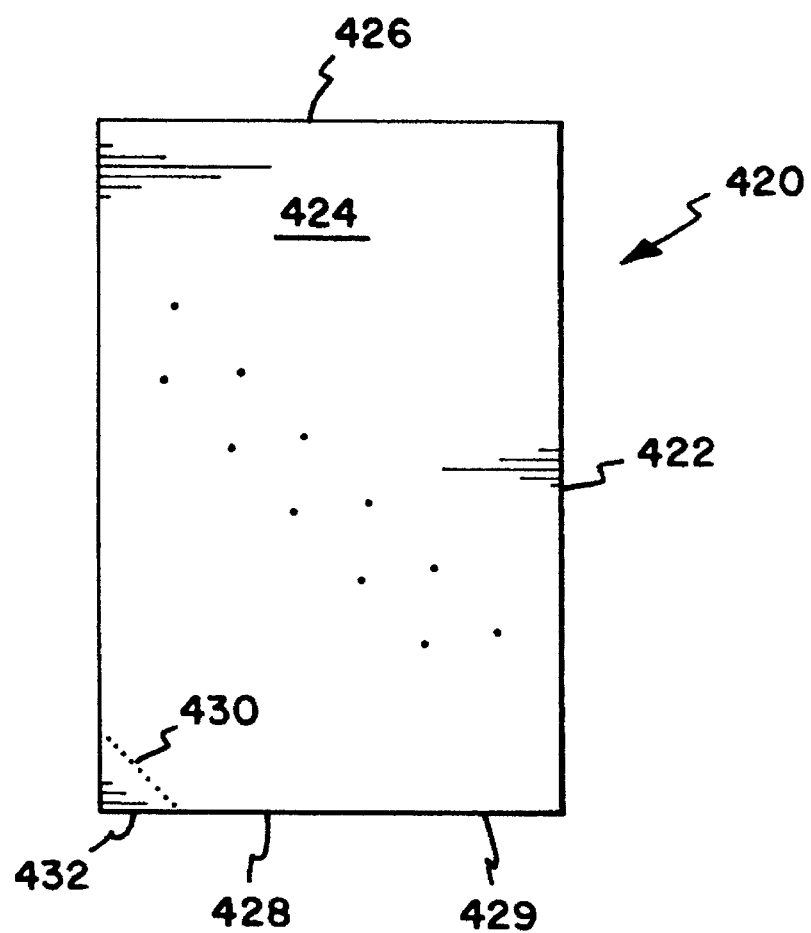
FIG. 18 is a third alternative embodiment of a bag arrangement to the arrangement shown in FIG. 1.

Referring now to FIG. 18, a third alternative bag 420 is shown. A peripheral edge 422 joins a front panel 424 to a back panel (not visible) along peripheral edge 422 except along linear top edge 426. Peripheral edge 422 defines a converging tip 428. Perforation line 430 through both panels permits tip 432 to be torn away from a remainder of bag 420 for removal. Bag 420 is heat sealed along bottom edge 429. One advantage of bag 420 is that any perforations to permit separation of bag 420 from other bags in a roll stock arrangement need only be linearly arranged in a direction perpendicular to the longitudinal direction of bag 420 adjacent top edge 426 and bottom edge 429. Perforation line 430 is arranged at an angle of 45 degrees to the longitudinal direction.

Bag 20, and any alternative configurations, can be made from a variety of materials including various plastics. Preferably bag 20 is made from a clear plastic material, or alternatively one sufficiently transparent to visible light to permit viewing of the contents within the bag. A 1 mil thick bag made from a polymeric material, such a polyethylene with EBA works well. A thicker material, such as 2 mil, also works. Bag 20 having dimensions of open top end to closed bottom end of about 8 inches and a width of about 4 inches works well for hand mixing of dental alginates for a single patient use. A ⅛ inch seal provided by heat sealing is supplied at closed end 36 of bag 20.

Bag 20 and the other bags of the invention are made from sufficiently flexible material such that bag 20 can be closed by twisting the bag shut. Such twisting action can be used in lieu of a separate closure device or in combination with a closure device. The closure device can be added after twisting the bag shut and hand mixing. If a roll stock arrangement is used, it is anticipated that any closure device be reusable such that a single closure device or just a few be packaged with a roll stock arrangement of bags 20, such as in a 50 or 100 count roll.

Bag 20 and the other bags of the invention can be prepackaged with a metered amount of powder, such as alginate powder or other, such that a user only needs to add a specific amount of fluid, such as water, to make the mixture using bag 20.

Indicia can be provided on bag 20 and the other bags of the invention to indicate appropriate powder and fluid levels to be added by the user.

Perforation line 48 of bag 20, associated with the removable tip of bag 20 and second perforations 49, and the perforations of the separation lines 45a, 45b between bags 20, 20a, 20b, and the other bags of the invention can be made by various manufacturing processes, including piercing with a pin or a cutting blade. It is preferred that the tear strength of perforation line 48 be stronger than separation line 45a, 45b such that perforation line 48 will not be inadvertently torn when separating bag 20 from an adjacent bag 20a, 20b.

One preferred use of bag 20, and the other bags of the invention is to mix dental alginates and stones. Some examples of alginates that work with the present invention include: SURGIDENT (registered trademark) ORTHO GEL (tm) by Columbus Dental of St. Louis, Mo.; JELTRATE (registered trademark) plus (tm), by the L. D. Caulk Division, Dentsply International, Inc., Milford, Del.; ALGINATE COE (registered trademark) COE HYDROPHILIC GEL (tm), Coe Laboratories, Inc., Chicago, Ill.; and Identic Dental Alginate Impression Material, Cadco,, Oxnard, Calif. Other mixtures can be made using the bags, and closure devices and techniques, such as mixing other hardenable construction materials such as plasters and mixing powdered foods.

The present invention permits dental alginates, and other mixable powders to be mixed quickly and in a consistently good manner without significant training, cost, or mess. In the case of dental alginates, the bags permit quick dispensing of the soft alginate to the trays in a clean and accurate manner. Once the contents are dispensed, the bag is discarded after use, allowing for quick clean up. In the case of needing to make a plurality of dental impressions quickly and efficiently for a large group of people, such as a sports team who requires individually fitted mouthguards for team members, the bags provide convenient structure for efficiently mixing the ingredients, dispensing the mixed ingredients, and cleaning up afterwards. The dentist and the dental assistants can make the necessary molds in an assembling line fashion, saving time and money from conventional methods.

It must be understood, however, that even though numerous advantages and characteristics of the invention have been set forth in the foregoing description together with details of the structure and function of the invention, the disclosure is illustrative only, and changes may be made in detail, especially in matters of shape, size and material components within the principals of the invention, to the full extent indicated by the broad, general meanings of the terms in which the appended claims are expressed.

What is claimed is:

1. A mixing bag arrangement for mixing ingredients comprising:

first and second panels each having an outer peripheral edge;

the first panel interconnected to the second panel along a first portion of each outer peripheral edge of each of the first and second panels to define an enclosed chamber for receiving the ingredients;

the enclosed chamber accessible through an open end defined by a second portion of each outer peripheral edge which is not interconnected to one another;

the first portion of each peripheral edge including a region defining a converging tip disposed on an opposite end of the panel arrangement relative to the open end; and the first and second panels each including a line of perforations extending across the converging tip of each of the first and second panels permitting a dispensing opening to be formed therein when the line of perforations is torn, to dispense the ingredients from the enclosed chamber, the line of perforations extending across both of the first and second panels which define the enclosed chamber.

2. The mixing bag arrangement of claim 1, wherein the second portion of each peripheral edge defines a first shape, and a part of the first portion of each peripheral edge defines a reciprocal shape to the first shape.

3. The mixing bag arrangement of claim 1, wherein the first and second panels each include perforations spaced apart from the line of perforations.

4. The mixing bag arrangement of claim 1, further comprising closure means for closing the opening.

5. The mixing bag arrangement of claim 1, further comprising a hardenable construction material disposed in the enclosed chamber.

6. The mixing bag arrangement of claim 1 wherein:

the outer peripheral edge of each of the first and second panels has two opposed side edges, a top edge, and a bottom edge, each of the top edge and the bottom edge extending between the two side edges of each panel;

the first panel interconnected to the second panel along each of the two side edges and each bottom edge to define the enclosed chamber;

the bottom edge of each of the first and second panels defines the converging tip;

the top edge of each of the first and second panels defines a reciprocal shape to the bottom edge of each of the first and second panels; and the first panel and the second panel are made of a polymeric material which is at least partially transparent to visible light.

7. The mixing bag arrangement of claim 6, wherein the bottom edge of each of the first and second panels includes two linear portions which intersect at a region located along a central longitudinal axis of each panel.

8. The mixing bag arrangement of claim 7, wherein the first and second panels each include perforations spaced apart from the line of perforations.

9. The mixing bag arrangement of claim 8, wherein the perforations spaced apart from the line of perforations includes two lines of perforations offset from one another in a direction parallel to the two lines of perforations.

10. The mixing bag arrangement of claim 6, further comprising closure means for closing the enclosed chamber from the top edge of each of the first and second panels.

11. The mixing bag arrangement of claim 10, wherein the closure means includes first and second members hingedly attached to one another, and snap means for releasably locking a free end of each of the first and second members relative to one another.

12. The mixing bag arrangement of claim 11, wherein at least one of the first and second members includes a rotatably mounted roller.

* * * * *